(12) United States Patent
Spahn

(10) Patent No.: US 7,496,223 B2
(45) Date of Patent: Feb. 24, 2009

(54) IMAGING DEVICE INCLUDING OPTIMIZED IMAGING CORRECTION

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 817 days.

(21) Appl. No.: 11/021,784

(22) Filed: Dec. 22, 2004

(65) Prior Publication Data

US 2005/0151086 A1 Jul. 14, 2005

(30) Foreign Application Priority Data

Dec. 29, 2003 (DE) ................ 103 61 397

(51) Int. Cl.
*G06K 9/00* (2006.01)
*G06K 9/40* (2006.01)
(52) U.S. Cl. ...................... 382/132; 382/275
(58) Field of Classification Search ........... None
See application file for complete search history.

(56) References Cited

U.S. PATENT DOCUMENTS

| 4,975,935 | A | 12/1990 | Hillen et al. |
| 5,923,722 | A | 7/1999 | Schulz |
| 5,969,360 | A | 10/1999 | Lee |
| 2003/0146390 | A1* | 8/2003 | Vafi et al. ............. 250/370.15 |
| 2003/0210762 | A1 | 11/2003 | Spahn |
| 2003/0223539 | A1* | 12/2003 | Granfors et al. ............ 378/98.8 |

FOREIGN PATENT DOCUMENTS

| DE | 196 31 624 C1 | 10/1997 |
| DE | 197 51 107 A1 | 6/1998 |
| DE | 197 51 298 A1 | 6/1998 |
| DE | 102 13 564 A1 | 10/2003 |

\* cited by examiner

*Primary Examiner*—Charles Kim

(57) ABSTRACT

In order to eliminate ghost effects, offset images (16, 17) are recorded in an imaging device with an x-ray detector immediately before and after the recording of an x-ray image (10), and, from said offset images (16, 17), an optimized offset image (19) is calculated which can be used to calculate an x-ray image (21) that is free from ghost effects.

6 Claims, 2 Drawing Sheets

IMAGING DEVICE INCLUDING OPTIMIZED IMAGING CORRECTION

CROSS REFERENCE TO RELATED APPLICATIONS

This application claims priority to the German application No. 10361397.8, filed Dec.29, 2003 which is incorporated by reference herein in its entirety.

FIELD OF INVENTION

The invention relates to an imaging device having a detector for recording object images with the help of high-energy photons and having an evaluation unit, which corrects the object images with the help of correction images, connected in series to the detector.

BACKGROUND OF INVENTION

Imaging devices of this type are generally known in the form of x-ray machines. X-ray machines for digital X-ray imaging are currently being developed. The new-style x-ray machines for digital x-ray imaging use so-called flat-panel detectors (among other things) that can be classified as flat-panel detectors with direct conversion and flat-panel detectors with indirect conversion.

Flat-panel detectors with indirect conversion have a scintillator extended over the surface, which covers a read-out matrix made from amorphous silicon. Various materials may be used for the scintillator. Materials normally used are manufactured on the basis of CsI or $Gd_2O_2S$. The read-out matrix comprises a plurality of photodiodes which convert the light generated in the scintillator from incident x-rays, into electrical charges. These electrical charges are stored in the capacitors allocated to each of the individual photodiodes, and, after the recording process is complete, are read out by active switching elements and converted into digital data with the help of analog-digital converters.

In flat-panel detectors with direct conversion, the incident x-rays are converted into electrical charges in a photoconductive layer, which is typically made from amorphous selenium. The electrical charges are stored in electrodes adjoining the photoconductive layer, and then read out from the electrodes with the help of active switching elements.

SUMMARY OF INVENTION

So-called ghost effects, leading to ghost images, may occur in flat-panel detectors with direct and indirect conversion. Ghost images are images that contain the signal of the current object image as well as images retained from earlier object images, whereby the current object image may be the x-ray image of a patient or other object, or may even be a darkframe. Image retention from previous object images sometimes seriously distorts the current object image, sometimes resulting in the current object image being incorrectly interpreted. It is therefore desirable to suppress the ghost effects as far as possible so that they are no longer perceptible.

This object is achieved by the claims. Advantageous embodiments and developments are described in the independent claims.

The imaging device is characterized in that at least two correction images are captured in conjunction with the recording of an object image, and in that the evaluation unit calculates, from the correction images, a correction image that is optimized to the point in time at which the object image is recorded, such that said correction image may be used to correct the assigned object image.

By recording two correcting images in conjunction with the recording of an object image, it is possible to determine the chronological sequence of the retained images and to calculate a correction image that corresponds to the actual images retained at the point in time when the object image was recorded. The retained images can thus be eliminated from the detector image. In this way it is possible to reconstruct an object image that is largely free from image retention.

In a preferred embodiment of the imaging device the correction image is an offset image, which shows the offsets from individual detector elements of the imaging device. The offset images are preferably recorded immediately before and after the object image is recorded, so that the correction image can be determined through interpolation, with a high degree of accuracy, at the point in time when the correction image is recorded.

In a further preferred embodiment, provision is made for the correction images to be averaged with a weighting factor. This weighing factor can be determined by trials and can be fixed according to each embodiment of the imaging device. In this way, calculation of the current correction image is greatly simplified.

In a further preferred embodiment, the weighting of the correction images takes into account the length of the interval between the recording of the respective correction image and the recording of the object image. This significantly increases the accuracy of the correction, particularly if the imaging device is operated asynchronously.

BRIEF DESCRIPTION OF THE DRAWINGS

Other features and advantages of the imaging device are explained in the following description, in which exemplary embodiments of the invention are described in detail. In the diagrams.

DETAILED DESCRIPTION OF INVENTION

Figure 1:
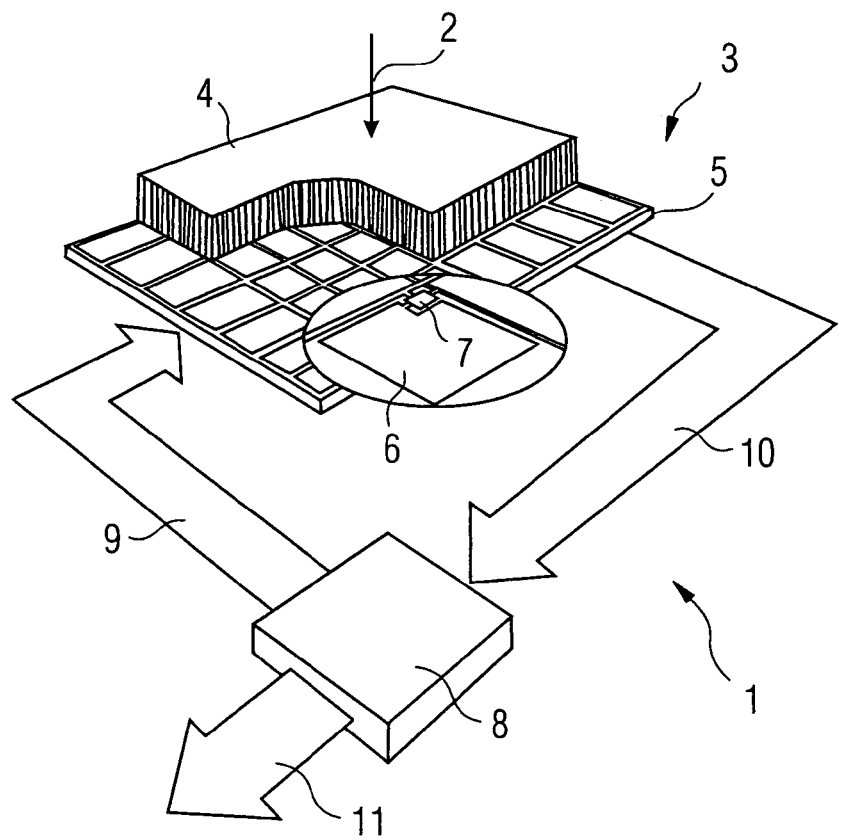
FIG. 1 is a perspective view of an imaging device equipped with a flat-panel detector.

FIG. 1 shows an imaging device 1, which is part of an x-ray device and which incorporates an x-ray source (not shown in FIG. 1) for generating x-rays 2. The x-rays 2 fall on a flat-panel detector 3 after passing through an object to be radiographed. The flat-panel detector 3 typically measures about 30 cm by 30 cm. The flat-panel detector 3 incorporates a scintillator 4, which is manufactured—for example—from CsI. Below the scintillator 4, there is an active matrix 5, which is normally manufactured on the basis of amorphous silicon. A field of photodiodes 6 is formed on the active matrix 5. In the photodiodes 6, the light generated in the scintillator 4 via the respective photodiode 6 is absorbed and electron-hole pairs are generated, which migrate in turn to the anode and cathode of the respective photodiode 6. The charge thus generated is stored in the respective photodiode 6 until said photodiode 6 is read out with the help of an active switching element 7. The active switching elements 7 are activated in rows by an evaluation unit 8 with the help of address data 9 and read out in columns, with said evaluation unit 8 having raw digital data representing an unprocessed x-ray image applied to it.

It is expressly noted that the term evaluation unit 8 describes the function of the said unit. The evaluation unit 8 does not necessarily have to be implemented as an individual semiconductor element. The evaluation unit 8 might rather incorporate a plurality of semiconductor elements from one or more printed circuit boards. The evaluation unit 8 may also include functional groups in different devices. The purpose of the evaluation unit 8 is to control and monitor the flat-panel detector 3. The evaluation unit 8 may also have the task of generating, from the raw data, a digital x-ray image 11 suitable for diagnostic purposes and outputting this image to a display unit 1 (not shown in FIG. 1).

Figure 2:
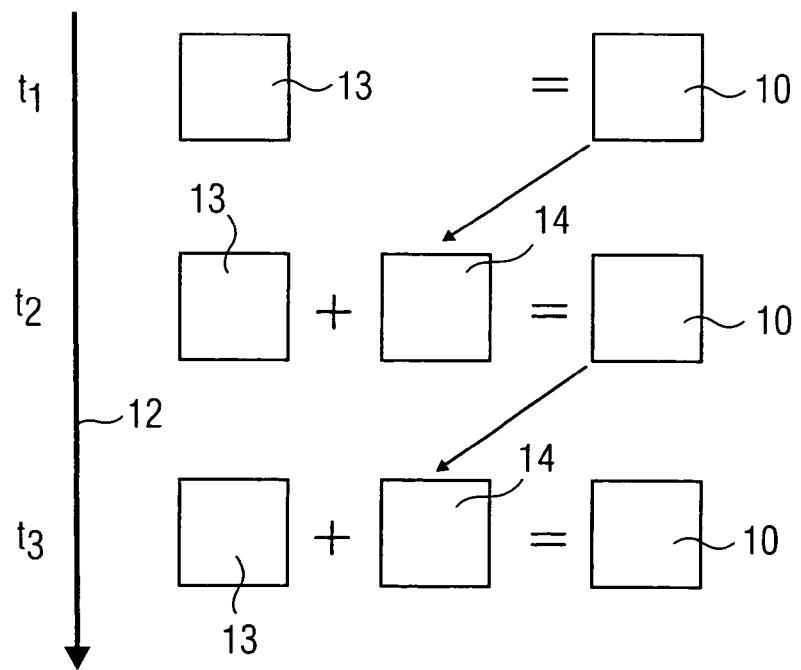
FIG. 2 is a diagram illustrating the effect of image retention on the x-ray images recorded.

FIG. 2 illustrates the occurrence of ghost images. This diagram shows, among other things, a time line 12, which illustrates the passage of time. Unprocessed x-ray images 10 are supplied from the flat-panel detector 3 at the points in time $t_1$, $t_2$ and $t_3$. At the point in time $t_1$ the unprocessed x-ray image 10 corresponds to a detector image 13, which is free from image retention from previously recorded images, even though it may be impaired by detector effects such as variations in intensity in the individual detector elements of the flat-panel detector 3 or offsetting variations in the individual detector elements.

At the point in time $t_2$, the unprocessed x-ray image 10—which was recorded at the point in time $t_1$—has already been read out from the flat-panel detector 3. If the flat-panel detector 3 is read out again at the point in time $t_2$ without being exposed again to x-rays 2, a residual image 14 would be read out that contains the retained images of the unprocessed x-ray image 10. However, since the flat-panel detector 3 has already been exposed again to the x-rays 2 at the point in time $t_2$, the unprocessed x-ray image 10 at the point in time $t_2$ is a superimposition of the residual image 14 that contains the retained images of the previously completed x-ray image 10, and of the detector image 13 that incorporates the structural information of the radiographed object together with the impairments caused by detector effects.

The same applies at the point in time $t_3$. The unprocessed x-ray image 10 that is read out at the point in time $t_3$ following a repeat exposure of the flat-panel detector 3 to the x-rays 2, incorporates the detector image 13 recorded at the point in time $t_3$ as well as the residual image 14. The residual image 14 at the point in time $t_3$ contains the retained images of the unprocessed x-ray image 10 that was read out at the point in time $t_2$, whereby said unprocessed x-ray image 10 in turn contains the residual image 14 at the point in time $t_2$ with the retained images of the unprocessed x-ray image 10 read out from the flat-panel detector 3 at the point in time $t_1$. The residual image at the point in time $t_3$ is thus a superimposition of the retained images of the x-ray images 10 read out at the points in time $t_1$ and $t_2$.

The intensity of the image retention depends partly on the technical conditions of the flat-panel detector 3. For example, the material characteristics of the flat-panel detector 3 may affect the characteristics of the residual image 14. The intensity of the residual image 14 is, however, determined by the x-ray 2 dose applied and the time that has elapsed since the application of x-rays 2. This is because the intensity of the residual image 14 diminishes over time. The decrease in intensity of the residual image 14 is typically described by an exponential function.

Since the intensity of the residual image 14 also depends on the intensity of the x-rays 2 incident upon the flat-panel detector 3, the residual image 14 may have roughly the same intensity locally as the detector image 13. For example, if organs such as the thorax, the pelvis or lateral spinal column are exposed to x-rays, the local doses incident upon the flat-panel detector 3 vary considerably between the area of the organ and the area beside the organ. In areas in which the x-rays 2, without shading, are directly incident upon the flat-panel detector 3 after passing through the organ to be examined or through apertures used to guide the radiation, the x-ray dose may be up to or more than 100 times greater than in the area inside or below the object or organ. Therefore, if the intensity of the residual image 14 has subsided, after a certain period has elapsed, to 1 percent of the intensity of the original x-ray image 10, then the intensity of the residual image 14 in the directly exposed area remains as great as the intensity of the detector image 13 in the area of the organ or object to be examined.

Figure 3:
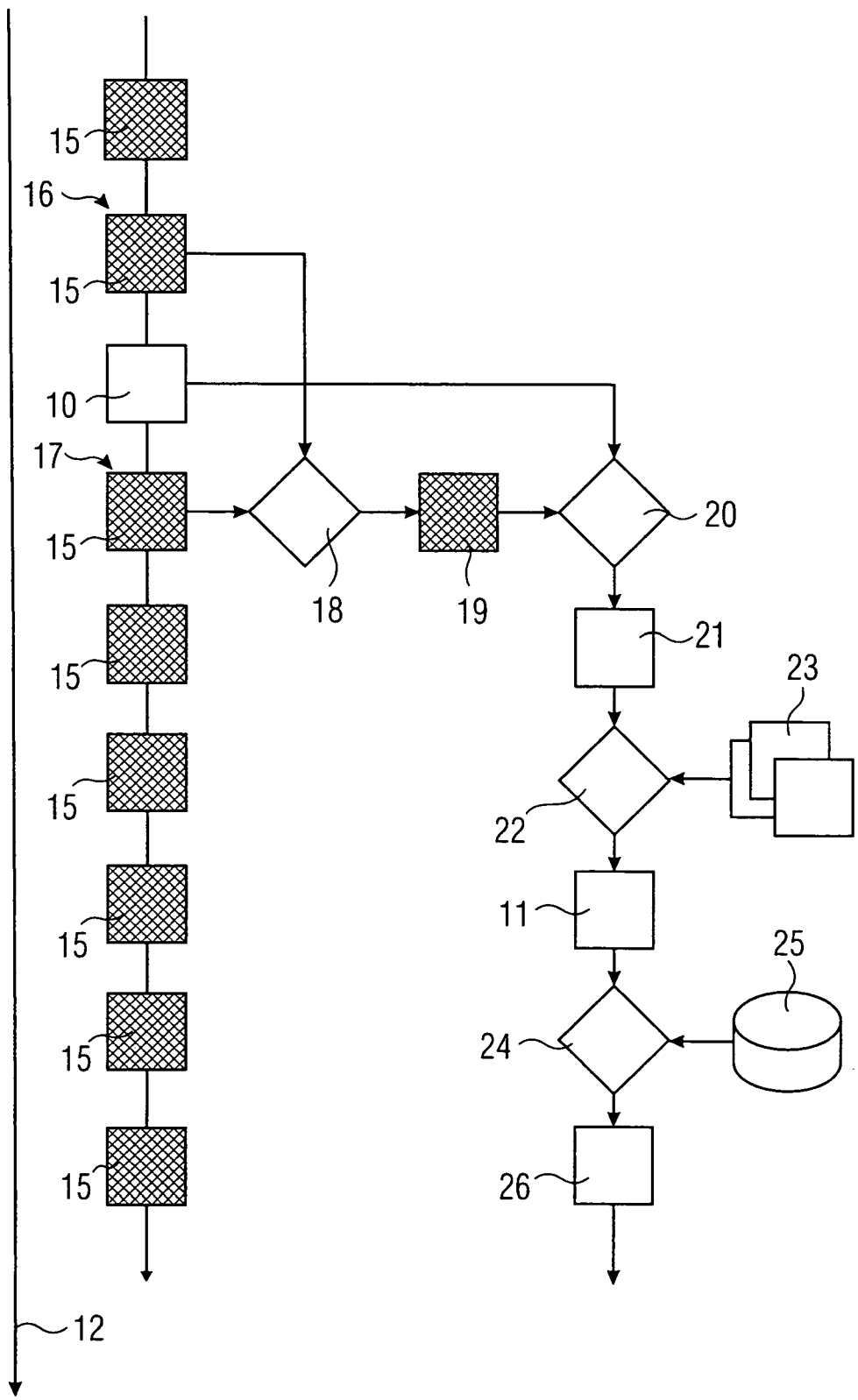
FIG. 3 is a flow chart illustrating the sequence of the correction process carried out by the evaluation unit of the imaging device.

FIG. 3 illustrates the sequence of a correction process carried out in the evaluation unit 8. So-called offset images 15 are recorded consecutively by the imaging device 1. The offset images are recorded without incident x-rays 2 and reflect the offsets of the detector elements of the flat-panel detector 3 that are formed by the photodiodes 6. If the flat-panel detector 3 contains a residual image 14 of a previous x-ray image 10, the offset image 15 also contains the residual image 14.

According to the correction process shown in FIG. 3, a first offset image 16 and a second offset image 17 are recorded around the same time that the x-ray image 10 is recorded. The first offset image 16 is preferably captured immediately before the recording of the x-ray image 10 and the second offset image 17 immediately after the recording of the x-ray image 10. However, it is also always possible for the first offset image 16 and the second offset image 17, which are used to correct the x-ray image 10, both to be captured immediately before or after the x-ray image 10 is recorded.

A first arithmetic unit 18 calculates an optimized offset image 19 from the first offset image 16 and the second offset image 17, whereby said optimized offset image 19 corresponds largely to the actual offset at the time when the x-ray image 10 was recorded. With the help of the optimized offset image 19, an offset-corrected x-ray image 21 containing minimal residual image 14 content is generated in a second arithmetic unit 20.

The fully corrected x-ray image 11 is then generated in a third arithmetic unit 22 with the help of further correction images 23, such as—for example—gain images or defect images. This fully corrected x-ray image 11 can subsequently be converted, in a fourth arithmetic unit 24, into a required organ view 26 depending on the predefined parameters 25. In the fourth arithmetic unit 24, for example, filter functions, image rotations or automatic windowing are carried out depending on organ-specific parameters.

The correction process described on the basis of FIG. 3 is suitable both for synchronously and asynchronously operating imaging devices 1. In synchronously operating imaging devices 1 an x-ray image 10 or an offset image 15 is constantly recorded. The recording of x-ray images 10 and of offset images 15 takes place with fixed integration times at predefined intervals. For example, either one x-ray image 10 or one offset image 15 is recorded per second in imaging devices 1 that are used for radiography, or—in an imaging device used for fluoroscopy—30 x-ray images 10 or offset images 15, for example, are recorded per second. If the frequency for the x-ray images 10 or the offset images 15 is sufficiently high, the user does not notice any delay in the triggering of an x-ray recording 10. Furthermore, a first offset image 16 recorded shortly beforehand is always available for correcting the recorded x-ray image 10. The second offset image 17 is then recorded immediately after the recording of the x-ray image 10 is completed.

A linear combination of the first offset image 16 and the second offset image 17 is then calculated in the first arithmetic unit 18.

The optimized offset image 19 that is to be used for correcting the x-ray image 10 can be calculated from the first offset image and second offset image as follows:

$$\text{Offset}_{opt} = a \cdot \text{Offset}_1 + (1-a) \cdot \text{Offset}_2,$$

in which a is a real number between 0 and 1. The parameter a can be determined by trials and fixed during operation of the imaging device 1. However, it is also possible to allow the parameter a to vary depending on environmental conditions.

As already mentioned, the procedure described on the basis of FIG. 3 is also suitable for asynchronously operating imaging devices 1. When calculating the optimized offset image 19, however, it is necessary to take into account the length of the interval between the first offset image and the x-ray image 10 on the one hand, and between the x-ray image 10 and the second offset image 17 on the other. The optimized offset image 19 may be calculated as follows, for example:

$$\text{Offset}_{opt} = a(\Delta t_1, \Delta t_2) \cdot \text{Offset}_1 + (1-a(\Delta t_1, \Delta t_2)) \cdot \text{Offset}_2,$$

in which $0 < a(\Delta t_1, \Delta t_2) < 1$ and $\Delta t_1$ is the interval between the first offset image 16 and the x-ray image 10 and $\Delta t_2$ is the interval between the x-ray image 10 and the second offset image 17.

Ghost effects can be effectively suppressed in the imaging device 1. This is particularly advantageous in applications in which images are required rapidly in succession, for example applications in which x-rays are used in various energy fields, whole-body x-rays in which a plurality of x-ray images 10 have to be assembled, or even straightforward thoracic x-rays.

Furthermore, it is also noted that, in a modified embodiment, more than two offset images may be combined to generate an optimized off-set image. For example, it is possible—provided sufficient computing power is available—to use more than two offset images and to describe the process of the captured offsets using higher-order polynomials.

A feature of the interpolation process described here is its particularly high reliability. However, in principle it is also possible to carry out an extrapolation on the basis of at least two off-set images captured before or after the x-ray image is recorded.

Finally, it is noted that the imaging device 1 is not necessarily an imaging device with a flat-panel detector which converts the incident x-rays 2 indirectly into charge. The principles described here may also be used in imaging devices having flat-panel detectors with direct conversion.

The invention claimed is:

1. An imaging device, comprising:
    a detector for recording an object image using high-energy photons; and
    an evaluation unit connected to and arranged downstream of the detector for correcting the object image using correction images, wherein the imaging device captures at least two correction images related to the recorded object image, wherein the two correction images are recorded as the object image is recorded and the evaluation unit generates an optimized correction image using the at least two correction images, the optimized correction image related to a point in time when the object image was recorded, wherein the evaluation unit is configured to generate the optimized correction image by deriving an estimation based on the first and second correction images; wherein the evaluation unit process the first and second correction images using a weighting algorithm involving a weighted factor, the weighting factor based on respective time intervals between the point in time when the object image was recorded and the respective points in time when the first and second correction images were recorded.

2. The imaging device according to claim 1, wherein the at least two correction images are offset images.

3. The imaging device according to claim 1, wherein the imaging device captures a first correction image before recording the object image and a second correction image after recording the object image and the estimation for generating the optimized correction image is derived by way of an interpolation algorithm based on the first and second correction images.

4. The imaging device according to claim 3, wherein the evaluation unit processes the first and second correction images using a weighting algorithm involving a pre-defined weighting factor.

5. The imaging device according to claim 1, wherein the imaging device captures both a first and second correction image either before or after recording the object image and the estimation for generating the optimized correction image is derived by way of an extrapolation algorithm based on the first and second correction images.

6. The imaging device according to claim 5, wherein the evaluation unit processes the first and second correction images using a weighting algorithm involving a pre-defined weighting factor.

* * * * *